United States Patent [19]

Bark

[11] Patent Number: 4,904,241
[45] Date of Patent: Feb. 27, 1990

[54] SEPTUM WITH A NEEDLE STOP AT THE FLUID TRANSFER PORT

[75] Inventor: Jeffrey E. Bark, Racine, Wis.

[73] Assignee: Medical Engineering Corp., Racine, Wis.

[21] Appl. No.: 262,145

[22] Filed: Oct. 21, 1988

Related U.S. Application Data

[63] Continuation of Ser. No. 919,905, Oct. 16, 1986, abandoned.

[51] Int. Cl.⁴ .............................................. A61M 11/00
[52] U.S. Cl. ...................................... 604/93; 604/117; 604/148; 604/175
[58] Field of Search ...................................... 604/8-10, 604/43, 175, 131, 891, 117, 148, 93

[56] References Cited

U.S. PATENT DOCUMENTS

| | | | |
|---|---|---|---|
| 3,310,051 | 3/1967 | Schulte | 604/175 |
| 4,190,048 | 2/1980 | Sampson | 604/175 |
| 4,344,435 | 8/1982 | Aubin | 604/175 |
| 4,364,395 | 12/1982 | Redmond et al. | 604/10 |
| 4,525,165 | 6/1985 | Fischell | 604/151 |
| 4,543,088 | 9/1985 | Bootman et al. | 604/175 |
| 4,544,371 | 10/1985 | Dormandy, Jr. et al. | 604/891 |
| 4,559,033 | 12/1985 | Stephen et al. | 604/93 |
| 4,588,394 | 5/1986 | Schulte et al. | 604/8 |
| 4,634,427 | 1/1987 | Hannula et al. | 604/93 |
| 4,710,174 | 12/1987 | Moden et al. | 604/244 |
| 4,784,646 | 11/1988 | Feingold | 604/9 |

FOREIGN PATENT DOCUMENTS

| | | | |
|---|---|---|---|
| 0134745 | 3/1985 | European Pat. Off. | 604/175 |
| 8316142 | 6/1983 | United Kingdom | 164/131 |

Primary Examiner—C. Fred Rosenbaum
Attorney, Agent, or Firm—Stuart E. Krieger

[57] ABSTRACT

The septum includes a fill chamber having a port that is reinforced or otherwise protected by a needle stop structure. The needle stop structure prevents a needle that has accessed the fill chamber from penetrating the fluid flow structure that extends from the fill chamber. In one embodiment of the invention, the needle stop structure overhangs the port thereby preventing a needle from entering the port. In a further embodiment of the invention the needle stop structure includes a nozzle-like annular collar which extends from the port into the fill chamber. In another embodiment of the invention, the needle stop structure includes a nozzle-like annular collar that extends from the port into the fluid flow structure. In yet another embodiment of the invention, the needle stop structure includes a cup-shaped structure that extends from the port into the fluid flow structure and has an opening in the fluid flow structure. In still another embodiment of the invention, the needle stop structure includes a conduit that extends from the port across the fill chamber. In all embodiments of the invention the needle stop structure is impermeable to penetrations by a needle and thus protects the fluid transfer structure from penetrations by a needle.

2 Claims, 3 Drawing Sheets

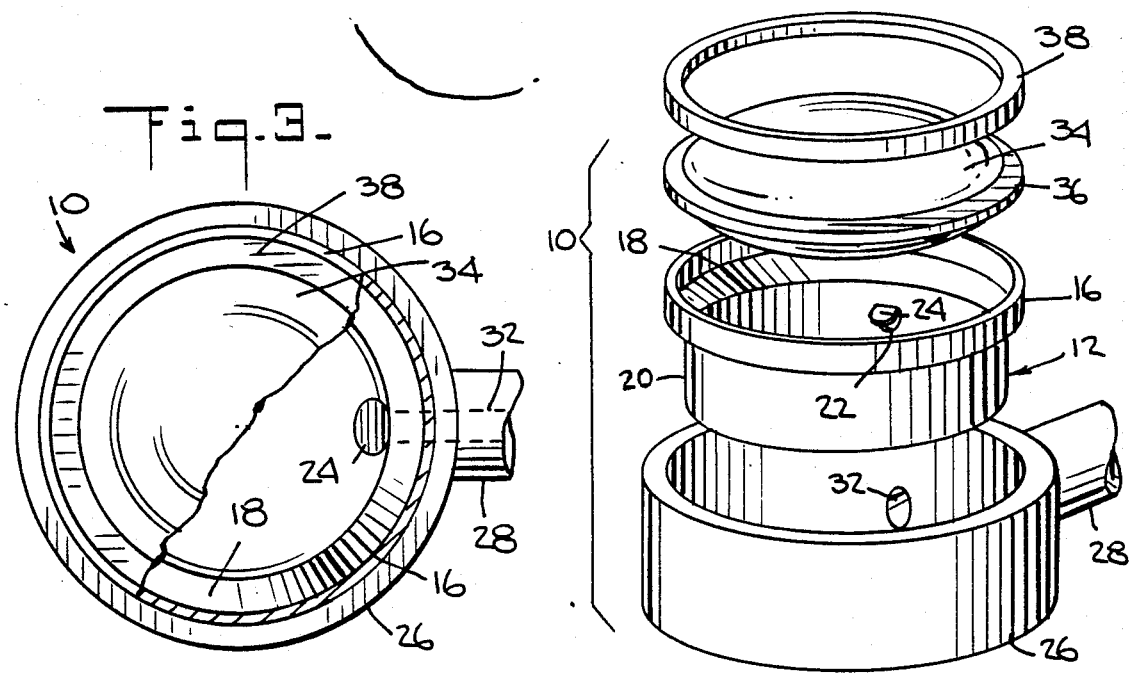
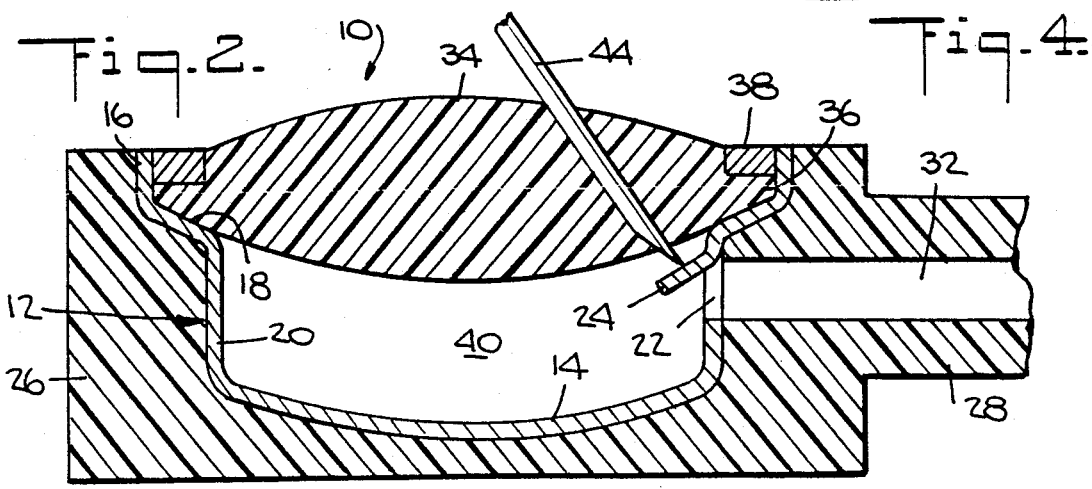

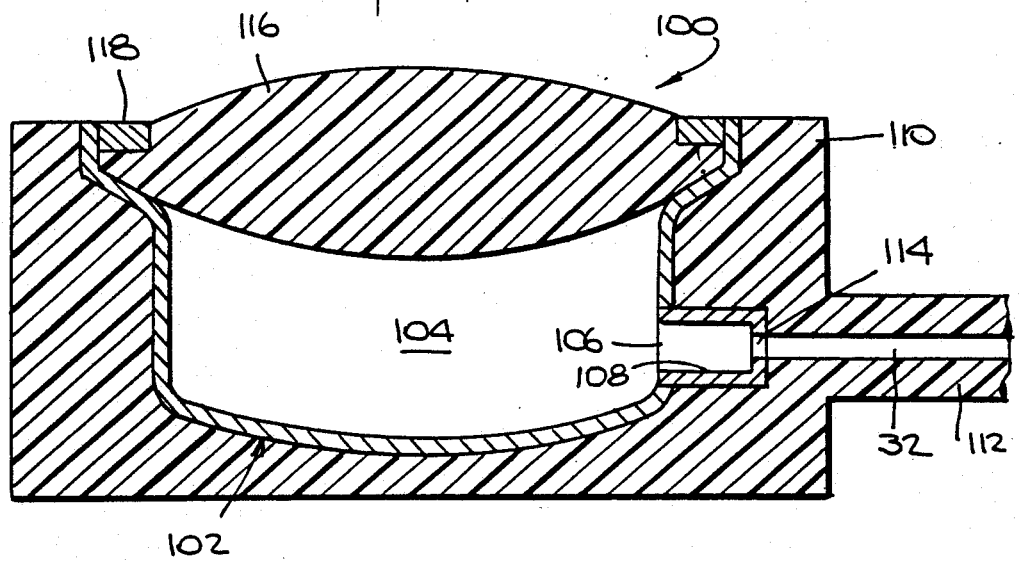
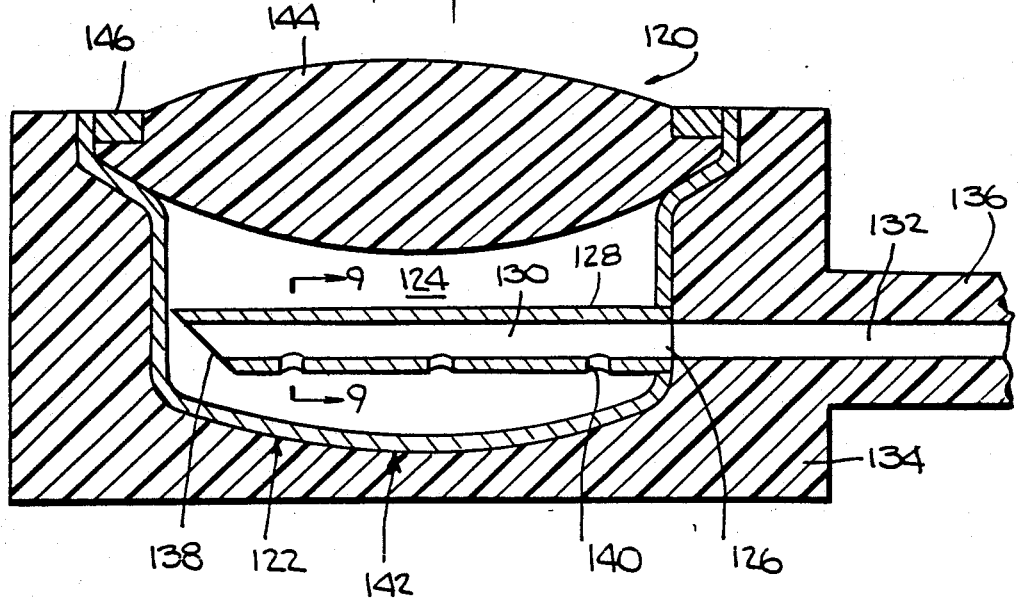
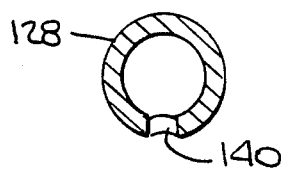

SEPTUM WITH A NEEDLE STOP AT THE FLUID TRANSFER PORT

This is a continuation of Ser. No. 919,905, filed Oct. 16, 1986, now abandoned.

BACKGROUND OF THE INVENTION

This invention relates to devices which operate with needles to transfer fluids to or from a prosthesis and more particularly to a septum with a novel needle stop arrangement that prevents a needle from penetrating a fluid transfer structure after the needle has accessed a fluid chamber of the septum.

As used herein the term "fluid transfer structure" relates to external fluid flow structure communicating with the fluid chamber of a septum.

Prosthetic devices implanted in the body to restore shapes and contours that have been surgically altered or accidentally deformed usually require infusions of fluid to restore proper pocket tension or to modify the shape or contour of the prosthesis. However it is normally not feasible to make direct access with a prosthesis for fluid infusions or fluid withdrawals due to the remote location of many prostheses and due to possible leakage problems that may develop if a prosthesis is penetrated by a needle.

Septums have thus become a well known vehicle for transferring fluid to a prosthesis through a fluid transfer structure and alternatively can be used to drain unwanted fluids from certain areas of the body. A septum, which is generally implanted near a prosthesis, usually includes a fluid chamber sealed by a needle penetrable seal member. Fluid is infused into or withdrawn from the fluid chamber by a hypodermic needle that accesses the fluid chamber through the needle penetrable seal member. The fluid transfer structure normally communicates with the fluid chamber and interconnects with the prosthesis.

Once a needle has penetrated the fluid chamber of a septum it is necessary to stop further movement of the needle in the septum to prevent the needle from passing completely out of the fluid chamber. It is thus well known to provide a needle stop member in a septum, usually at the base of the fluid chamber. The needle stop member is generally constructed of a needle impermeable material to prevent further movement of a needle out of the fluid chamber.

The fluid transfer structure which extends from the fluid chamber is usually formed of a relatively soft flexible material that does not resist penetration by a needle. Since the septum is normally implanted below the skin it is difficult to predetermine the path of the needle which accesses the fluid chamber. Thus the area of the septum where the fluid transfer structure joins the fluid chamber is vulnerable to penetrations by a needle if such needle is inadvertently oriented in a direction toward the fluid transfer structure during a fluid infusion or fluid withdrawal operation.

If a needle penetrates the fluid transfer structure after accessing the fluid chamber, the fluid transfer operation cannot be completed. Furthermore it may be difficult to detect when a needle has penetrated or passed through the fluid transfer structure, since such structure is implanted below the surface of the skin. Under these circumstances the person administering a fluid transfer operation is often not aware that fluid may be bypassing the fluid chamber.

It is thus desirable to provide a septum having a needle stop structure that prevents a needle in a fluid chamber from penetrating the fluid transfer structure and does not obstruct the flow of fluid into the fluid transfer structure.

OBJECTS AND SUMMARY OF THE INVENTION

Among the several objects of the invention may be noted the provision of a novel septum, a novel septum having a needle stop structure at the fluid chamber where a fluid transfer structure joins the fluid chamber, a novel septum having a needle stop structure that prevents movement of a needle from a fluid chamber into a corresponding fluid transfer structure yet does not obstruct flow from the fluid chamber into the fluid transfer structure, a novel septum having a needle stop structure that prevents a needle from passing out of the fluid chamber and also prevents a needle from passing into the fluid transfer structure, and a novel method of making a septum.

Other objects and features of the invention will be in part apparent and in part pointed out hereafter.

The septum, in accordance with one embodiment of the invention, includes a means for accumulating fluid such as a fluid or fill chamber that is sealed by a needle penetrable seal member. The fill chamber also includes a port for inlet or outlet of fluid. The needle penetrable seal member permits outside access to the fluid chamber upon penetration by a needle. Fluid flow means extend from the port of the fluid chamber and include a flow defining structure to establish a flow path to or from the fluid chamber. A needle stop means is provided in the fluid chamber in the vicinity of the port where the fluid flow means communicates with the fluid chamber. The needle stop means prevents a needle that accesses the fluid chamber through the sealing means from penetrating the flow defining structure in the vicinity of the port.

In one embodiment of the invention, the needle stop means comprises a impermeable flap member that overhangs the fluid flow port within the fluid chamber and thus prevents a needle from entering the flow path of the flow defining structure. Since the needle is prevented from entering the flow path of the fluid it cannot penetrate the flow defining structure.

If desired, the needle stop overhang can be formed as a portion of a needle stop member that lines the fluid chamber.

In another embodiment of the invention the needle stop structure which prevents a needle that accesses the fluid chamber from moving out of the fluid chamber into the flow defining structure includes an impermeable nozzle-like annular collar that extends into the fluid chamber from the port. The nozzle communicates with the flow defining structure and has a predetermined size and extent which prevents a needle that has accessed the fluid chamber from passing out of the fluid chamber through the port. The nozzle-like annular collar thus protects the flow defining structure from penetration by the needle.

In still another embodiment of the invention, an impermeable nozzle-like annular collar extends from the port of the fluid chamber into the fluid flow means, forming a protective liner for the flow defining structure. Thus, even if a needle which accesses the fluid chamber is directed toward the port, the nozzle prevents the needle from penetrating the flow defining structure.

In a further embodiment of the invention, an impermeable U-shaped nozzle extends from the port of the fluid chamber into the fluid flow means. An opening provided in the U-shaped nozzle permits the port of the fluid chamber to communicate with the fluid flow means. The nozzle opening is a predetermined size and distance from the port to assure that a needle accessing the fluid chamber cannot pass into or penetrate the flow defining structure.

In yet another embodiment of the invention, an impermeable conduit extends from the port of the fluid chamber into the chamber space. A surface of the conduit which is inaccessible to a needle is provided with openings that communicate with the fluid chamber port. Under this arrangement, the fluid chamber port is shielded by the conduit such that a needle which has accessed the fluid chamber cannot pass through the fluid port to the flow defining structure of the fluid flow means.

In all embodiments of the invention, the needle stop structure can be formed integral with a needle stop member that lines the interior of the fluid chamber.

The needle stop structure of the present invention thus provides assurance that a needle which accesses a fluid chamber will not penetrate the fluid transfer structure or become embedded in structure beyond the fluid chamber.

The invention accordingly comprises the constructions and the method hereinafter described, the scope of the invention being indicated in the claims.

DESCRIPTION OF THE DRAWINGS

In the accompanying drawings, in which several embodiments of the invention are illustrated, FIG. 1 is a simplified pictorial view of a septum incorporating one embodiment of the invention being used for infusing a prosthesis with a hypodermic needle;

FIG. 2 is a sectional view thereof;

FIG. 3 is a top plan view thereof, partly broken to clarify some structural details;

FIG. 4 is an exploded perspective view thereof;

FIGS. 5–8 are sectional views of other embodiments of the invention; and,

FIG. 9 is a sectional view taken on the line 9-9 of FIG. 8.

Corresponding reference characters indicate corresponding parts throughout the several views of the drawings.

DETAILED DESCRIPTION OF THE INVENTION

Figure 5:
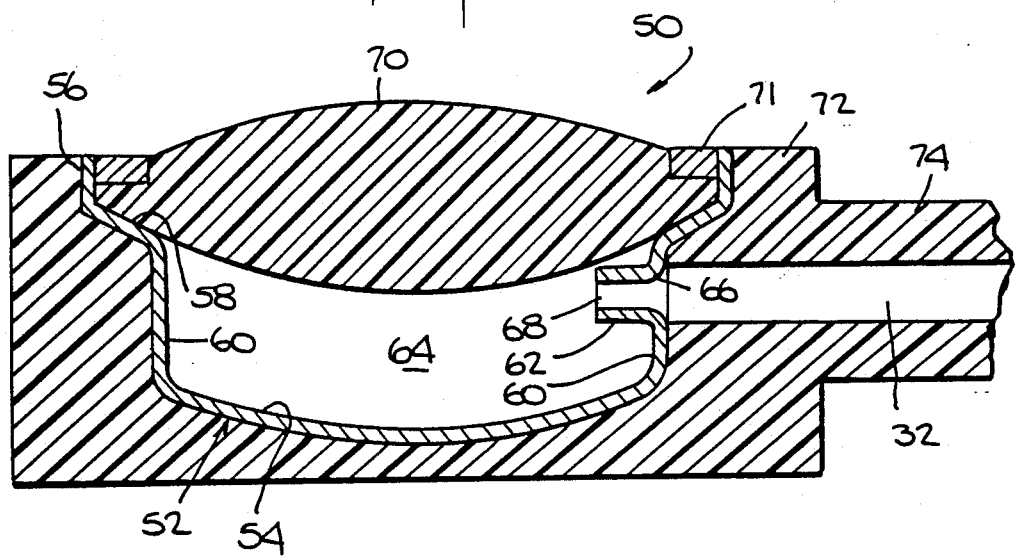

A septum incorporating one embodiment of the invention is generally indicated by the reference number 10. The septum 10 comprises a generally cup-shaped needle stop member 12 having a base 14 which can be of spherical contour.

The needle stop member 12 is preferably formed of stainless steel and has a mouth portion defined by a peripheral wall section 16. An inclined support surface 18 extends from the wall section 16, and a depending wall section 20 extends from the inclined support surface 18 to the base 14.

A fluid transfer port or opening 22 is provided in the wall section 20. A flap-like needle stop section 24, which can be formed from a portion of the wall section 20, extends over the fluid transfer opening 22.

A jacket section 26 preferably formed of a silicone elastomer is molded or otherwise provided in leak-tight arrangement around the needle stop member 12. A fluid transfer tube 28, which can be integrally molded with the jacket section 26, extends from the jacket section 26 to a prosthesis 30, partially shown in dotted outline in FIG. 1. A fluid passage 32 extends from the fluid transfer opening 22 through the jacket section 26 and the tube 28. The tube 28 and a portion of the jacket section 26 thus constitute the flow defining structure of the fluid passage 32.

A dome-shaped needle penetrable seal member 34, preferably formed of a silicone elastomer and having a reduced peripheral section 36 is disposed on the inclined support surface 18 of the needle stop member 12. A clamping ring 38, which is threaded, staked, press-fit or otherwise secured to the wall section 16, presses the edge portion 36 of the seal member 34 against the support surface 18 to accomplish a leak-tight seal. The reduced peripheral edge portion 36 of the seal member 34 thus functions as a sealing gasket.

Under this arrangement, the space encompassed by the needle stop member 12 and enclosed by the seal member 34 constitutes a fluid chamber or fill chamber 40 (FIG. 2) of the septum 10.

In using the septum 10, an implantation thereof is made under the surface of the skin (not shown) with the fluid transfer tube 28 directed toward the prosthesis 30. The septum 10 can be located before a fluid infusion or fluid withdrawal operation by palpating the skin which covers the area of the septum 10.

A syringe 42 containing a desired fluid is directed toward the septum 10 to permit the needle 44 to penetrate the seal member 34.

Once the needle 44 accesses the fluid chamber 40, there can be no further needle penetration beyond the fluid chamber. For example, the wall section 20 of the needle stop member 12 will prevent the needle 44 from penetrating the jacket section 26 from the fluid chamber 40. Furthermore, the base 14 of the needle stop member 12 will likewise prevent the needle from penetrating the jacket after accessing the fluid chamber 40.

An area of previous vulnerability to needle penetrations had been the fluid transfer opening 22. This area is no longer subject to needle penetrations due to the presence of the needle stop flap 24 which projects over the fluid transfer opening 22. Thus, even if the needle 44 is inadvertently directed toward the fluid transfer opening 22 as shown in FIG. 2, the needle stop flap 24 will deflect or otherwise prevent the needle 44 from entering the opening 22.

Under this arrangement, fluid infused into the chamber 40 by the syringe 42 is not obstructed from passing through the opening 22 into the fluid passage 32. The septum 10 is capable of resisting needle penetrations beyond the fluid chamber 40 even when the needle 44 is inadvertently directed toward the fluid transfer opening 22. The integrity of the flow defining structure, which includes the portion of the jacket 26 surrounding the passageway 32 and the fluid transfer tube 28, is thus maintained.

Another embodiment of the septum is generally indicated by the reference number 50 in FIG. 5. The septum 50 includes a needle stop member 52 having a spherical base 54, a peripheral section 56 and an inclined support surface 58 identical to the corresponding structure of the needle stop member 12.

The needle stop member 52 further includes a depending wall section 60 extending from the inclined support surface 58 to the base 54. The wall section 60 includes an impermeable annular collar formation such as a nozzle 62 projecting into a fill chamber 64 of the septum 50 from a port 66. A nozzle opening 68 is defined at the end of the nozzle 62 within the fill chamber 64.

The septum 50 further includes a needle permeable seal member 70, a clamping ring 71, a jacket section 72 and a fluid transfer tube 74 identical to the seal member 34, clamping ring 38, jacket section 26 and fluid transfer tube 28 of the septum 10.

The septum 50 is used in a manner similar to that previously described for the septum 10. It will be noted that a needle (not shown) directed toward the port 66 cannot penetrate the nozzle 62. Furthermore, the diameter and extent of the nozzle 62 into the fill chamber 64 are predetermined such that even if a needle were directed toward the nozzle opening 68, it could not pass through the port 68 which is surrounded by the jacket section 72.

Under this arrangement, the nozzle 62 effectively prevents a needle from penetrating the jacket section 72 and the fluid transfer tube 74. The fluid transfer structure of the septum 50 is thus protected from penetration by a needle that has accessed the fill chamber 64.

Figure 6:
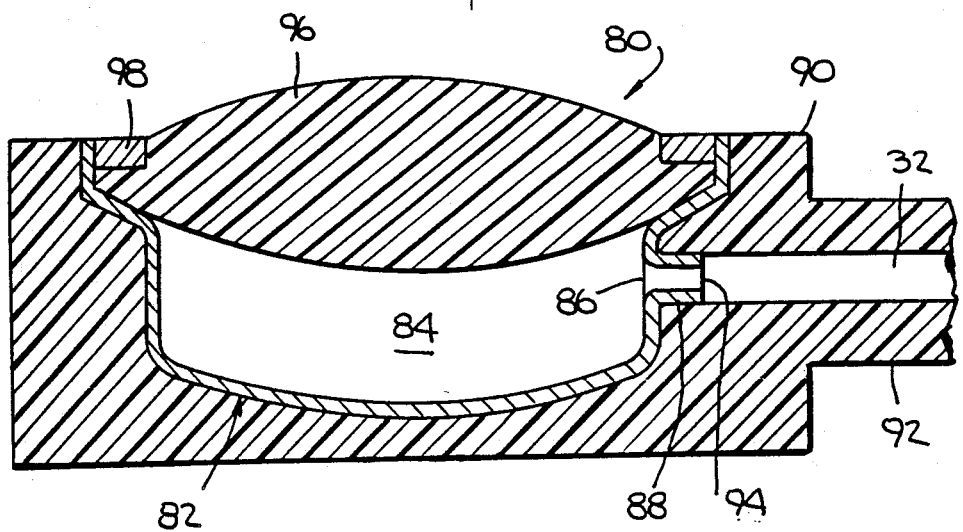

A further embodiment of the septum is generally indicated by the reference number 80 in FIG. 6. The septum 80 has a needle stop member 82 which lines a fill chamber 84 having a port 86. An impermeable annular collar formation such as a nozzle 88 extends from the port 86 outwardly of the fill chamber 84 into the passageway 32 of a jacket section 90 and a fluid transfer tube 92. The nozzle 88 has an opening 94 within the passageway 32. In all other respects, the needle stop member 82 is similar to the needle stop member 52.

The septum 80 further includes a needle penetrable seal member 96 and a clamping ring 98 identical to the seal member 34 and clamping ring 38 of the septum 10.

The septum 80 is used in a manner similar to that previously described for the septum 10. The nozzle 88 has a predetermined diameter and extent into the fluid transfer tube 92 that effectively prevents a needle (not shown) from extending beyond the opening 94 even if the needle has been inadvertently directed toward the fluid port 86. The flow defining structure 90 and 92 of the septum 80 is thus protected from penetrations by a needle that has accessed the fill chamber 84.

Another embodiment of the septum is generally indicated by the reference number 100 in FIG. 7. The septum 100 has a needle stop member 102 which lines a fill chamber 104 having a port 106. An impermeable annular collar formation, such as a nozzle 108, extends from the port 106 outwardly of the fill chamber 104 into the passageway 32 of a jacket section 110 and a fluid transfer tube 112. The nozzle 108 is U-shaped in cross-section and includes an opening 114 that forms a continuation of the passageway 32. In all other respects the needle stop member 102 is similar to the needle stop member 52.

The septum 100 also includes a needle penetrable seal member 116 and a clamping ring 118 identical to the seal member 34 and the clamping ring 38 of the septum 10.

The septum 100 is used in a manner similar to that described for the septum 10. The nozzle 108 has a predetermined diameter and extent to render the opening 114 virtually inaccessible to a needle (not shown) even though such needle might be inadvertently directed toward the port 106. Consequently the flow defining structure 110 and 112 of the septum 100 is out of range of a needle that has accessed the fill chamber 104. The flow defining structure 110 and 112 is thus protected from needle penetrations.

A further embodiment of the septum is generally indicated by the reference number 120 in FIG. 8. The septum 120 has a needle stop member 122 which lines a fill chamber 124 having a port 126. A conduit 128 extends from the port 126 across the fill chamber 124.

A passageway 130 in the conduit 128 communicates through the port 126 with a passageway 132 of a jacket 134 and a conduit 136. The conduit 128 terminates at an end 138 that is cut or formed at a predetermined angle with respect to its longitudinal axis (not shown) and bears against the needle stop member 122. The passageway 130 thus opens into the fill chamber 124 at the conduit end 138. A plurality of openings 140 provided in the conduit 130 face a base portion 142 of the needle stop member 122.

The septum 120 also includes a needle penetrable seal member 142 and a clamping ring 146 identical to the seal member 34 and the clamping ring 38 of the septum 10.

The septum 120 is used in a manner similar to that described for the septum 10. The conduit 128 shields the port 126 from a needle (not shown) that accesses the fill chamber 124. The opening 140 and the open end portion 138 of the conduit 128 permit communication between the fill chamber 124 and the passageways 130 and 132. Since the openings 140 of the conduit 128 face the base 142 of the needle stop 122, the passageway 130 is inaccessible to a needle (not shown) that enters the fill chamber 124 through the needle penetrable seal member 144. The port 126 and the flow defining structure 134 and 136 are likewise inaccessible to a needle and are thus protected from needle penetration.

It will be apparent that for each embodiment of the invention, a syringe needle can enter the fill chamber of the septum at an infinite number of angles and directions. However, only a limited range of access angles of the needle into the fill chamber will direct the needle toward the fluid transfer opening.

Thus the potential path of a needle to or beyond the fill port is either blocked from needle penetration or reinforced with a protective structure that inhibits or prevents a needle from penetrating the flow defining structure that extends from the fill port.

Some advantages of the present invention evident from the foregoing description include a septum that is completely protected in the vicinity of the fill port to prevent a needle from penetrating the fluid transfer structure that extends from the needle stop member. Consequently there can be reliability that a needle which has accessed the fill chamber of the septum will not penetrate the fluid transfer structure.

In view of the above, it will be seen that the several objects of the invention are achieved and other advantageous results attained.

As various changes can be made in the above constructions and method without departing from the scope of the invention, it is intended that all matter contained in the above description or shown in the accompanying drawings shall be interpreted as illustrative and not in a limiting sense.

What is claimed is:

1. A septum comprising,
   a cup-shaped needle stop member defining a central fluid chamber, said needle stop member including a base with a peripheral sidewall extending therefrom defining an open mouth portion, said sidewall having a port therein and a support surface,
   fluid flow means in communication with said port for establishing a fluid flow path with said fluid chamber, and
   a needle penetrable self-sealing member supported by said support surface and sealing said open mouth portion of said fluid chamber, said needle stop member including a needle stop portion at said port to prevent a needle accessing said fluid chamber through said self-sealing member from a penetrating said fluid flow means,
   said needle stop portion including a conduit extending from said port into said fluid chamber, said conduit being formed of a material impermeable to needles, and including openings remote from said needle penetrable sealing means such that said openings are inaccessible to a needle penetrating said sealing means.

2. A septum comprising,
   a cup-shaped needle stop member defining a central fluid chamber, said needle stop member including a base with a peripheral sidewall extending therefrom defining an open mouth portion, said sidewall having a port therein and a support surface, said sidewall also including a grooved portion,
   fluid flow means in communication with said port for establishing a fluid flow path with said fluid chamber, and
   a needle penetrable self-sealing member supported by said support surface and sealing said open mouth portion of said fluid chamber, said needle stop member including a needle stop portion at said port to prevent a needle accessing said fluid chamber through said self-sealing member from penetrating said fluid flow means.
   a ring-like clamp member for clamping said needle penetrable self-sealing member against said support surface, said clamp member screwing into the grooved portion of said sidewall.

* * * * *